United States Patent
Gooding et al.

(10) Patent No.: US 11,351,060 B2
(45) Date of Patent: Jun. 7, 2022

(54) INTERFACE FORCE FEEDBACK IN A LASER EYE SURGERY SYSTEM

(71) Applicant: OPTIMEDICA CORPORATION, Santa Ana, CA (US)

(72) Inventors: Phillip Gooding, Mountain View, CA (US); Bruce Robert Woodley, Palo Alto, CA (US)

(73) Assignee: AMO Development, LLC, Santa Ana, CA (US)

( * ) Notice: Subject to any disclaimer, the term of this patent is extended or adjusted under 35 U.S.C. 154(b) by 418 days.

(21) Appl. No.: 16/414,707

(22) Filed: May 16, 2019

(65) Prior Publication Data

US 2019/0274878 A1 Sep. 12, 2019

Related U.S. Application Data

(62) Division of application No. 14/069,582, filed on Nov. 1, 2013, now Pat. No. 10,292,863.

(60) Provisional application No. 61/721,709, filed on Nov. 2, 2012.

(51) Int. Cl.
*A61F 9/008* (2006.01)
*A61F 9/009* (2006.01)

(52) U.S. Cl.
CPC .............. *A61F 9/008* (2013.01); *A61F 9/009* (2013.01)

(58) Field of Classification Search
CPC . A61F 9/008; A61F 9/009; A61F 2009/00846
USPC ............................................................ 606/4
See application file for complete search history.

(56) References Cited

U.S. PATENT DOCUMENTS

| | | | |
|---|---|---|---|
| 4,517,973 A * | 5/1985 | Sunago | A61B 18/22 606/16 |
| 5,459,570 A | 10/1995 | Swanson et al. | |
| 5,720,894 A | 2/1998 | Neev et al. | |
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,053,613 A | 4/2000 | Wei et al. | |
| 6,111,645 A | 8/2000 | Tearney et al. | |
| 6,454,761 B1 | 9/2002 | Freedman | |
| 6,569,070 B1 | 5/2003 | Harrington et al. | |
| 7,402,159 B2 * | 7/2008 | Loesel | A61F 9/009 351/208 |

(Continued)

*Primary Examiner* — Aaron F Roane
(74) *Attorney, Agent, or Firm* — Johnson & Johnson Surgical Vision, Inc.

(57) ABSTRACT

The patient interface may comprise an axis for alignment with an axis of the eye such as an optical axis of the eye. The interface may comprise a guide to allow the interface to move along the axis with the eye, which can inhibit increases in intraocular pressure when the patient is aligned with the laser. The interface may comprise a lock to hold the patient interface at a location along the axis, which can maintain alignment of the patient with the laser eye surgery system. The interface may comprise a plurality of transducers to measure forces to the eye during surgery. The laser eye surgery system can be configured in one or more of many ways to respond to the measured forces. For example, the system may offset the position of laser beam pulses to increase the accuracy of the placement of the beam pulses on the eye.

19 Claims, 11 Drawing Sheets

(56) References Cited

U.S. PATENT DOCUMENTS

| | | |
|---|---|---|
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 8,864,757 B2 * | 10/2014 | Klimovitch ............ A61B 5/283 606/37 |
| 2009/0247997 A1 * | 10/2009 | Watanabe ........... A61F 9/00829 606/4 |
| 2010/0169815 A1 * | 7/2010 | Zhao ..................... A61B 34/35 715/771 |
| 2010/0274228 A1 | 10/2010 | Mrochen et al. |
| 2011/0319873 A1 | 12/2011 | Raksi et al. |
| 2011/0319875 A1 | 12/2011 | Loesel et al. |

* cited by examiner

INTERFACE FORCE FEEDBACK IN A LASER EYE SURGERY SYSTEM

CROSS-REFERENCE TO RELATED APPLICATIONS

This application claims priority to and is a divisional of U.S. patent application Ser. No. 14/069,582, filed Nov. 1, 2013, which claims the benefit of priority to U.S. Provisional Application No. 61/721,709, filed Nov. 2, 2012.

BACKGROUND

The present disclosure relates generally to laser eye surgery. Although specific reference is made to cataract surgery, the methods and apparatus described herein can be used with many surgical procedures of the eye and other tissues.

Many surgical procedures can be performed on patients, including ophthalmic surgery. Opthalmic surgery can include surgery on one or more of the cornea, the lens or the retina, for example.

Cataract extraction is a commonly performed surgical procedure. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). An estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy provides access for the next step of nuclear sculpting by phacoemulsification. Due to a variety of complications associated with the initial can-opener technique, attempts were made by leading experts in the field to develop a better technique for removal of the circular fragment of the anterior lens capsule prior to the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior lens capsule provides access for tool insertion during removal of the nucleus and for IOL insertion, a permanent aperture for transmission of the image to the retina of the patient, and also support of the IOL inside the remaining lens capsule that limits the potential for dislocation. The resulting reliance on the shape, symmetry, uniformity, and strength of the remaining lens capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the lens capsule due to lack of red reflex, to grasp the lens capsule with sufficient security, and to tear a smooth circular opening in the lens capsule of the appropriate size and in the correct location without creating radial rips and extensions. Also present are technical difficulties related to maintenance of the depth of the anterior chamber depth after opening the lens capsule, small pupils, or the absence of a red reflex due to the lens opacity. Some of the problems with visualization can be minimized through the use of dyes such as methylene blue or indocyanine green. Additional complications may also arise in patients with weak zonules (typically older patients) and very young children that have very soft and elastic lens capsules, which are very difficult to controllably and reliably rupture and tear.

The implantation of a "Bag-in-Lens" IOL typically uses anterior and posterior openings in the lens capsule of the same size. Manually creating matching anterior and posterior capsulotomies for the "Bag-in-Lens" configuration, however, is particularly difficult.

Many patients have astigmatic visual errors. Astigmatism can occur when the corneal curvature is unequal in two or more directions. In Astigmatic Keratotomy, Corneal Relaxing Incision (CRI), and Limbal Relaxing Incision (LRI), corneal incisions are made in a well-defined manner and depth to allow the cornea to change shape to become more spherical. These corneal incisions can accomplished manually but often with limited precision.

Although pulsed lasers have been proposed to treat eyes having cataracts and/or refractive errors, coupling of the prior patient interfaces can lead to less than ideal results in at least some instances. A patient interface can be provided to couple the laser beam to the eye to position the depth of the treatment within the eye at an intended location. However, the prior patient interfaces may provide less than ideal coupling of the eye to the laser. For example, prior patient interfaces can provide less than ideal increases in intra ocular pressure (hereinafter "IOP"). Also, the prior patient interfaces can be somewhat cumbersome for users of the system and the patients in at least some instances. Also, the prior patient interfaces can be somewhat rigid and intolerant of patient movement which may lead to decoupling of the interface and a partially completed treatment such that the prior patient interfaces may provide a less than ideal surgical experience in at least some instances.

Thus, improved methods and systems for treating are needed.

SUMMARY

Improved patient interface methods and apparatus are provided, which can facilitate alignment of the patient to the laser system and inhibit increases in intra-ocular pressure of the eye. The surgical laser system as described herein may comprise a patient interface assembly configured to inhibit increases of intraocular pressure during surgery, facilitate alignment during surgery, and can provide improved alignment of the patient. The patient interface may comprise an axis for alignment with an axis of the eye such as an optical axis of the eye. The patient interface may comprise a guide to allow the patient interface to move along the axis with the eye, which can inhibit increases in intraocular pressure when the patient is aligned with the laser. The patient interface may comprise a lock to hold the patient interface at a location along the axis, which can maintain alignment of the patient with the laser eye surgery system. The patient interface may comprise a plurality of transducers to measure forces to the eye during surgery, and the laser eye surgery system can be configured in one or more of many ways to respond to the measured forces. The laser eye surgery system may offset the position of the laser beam pulses in response to the measured forces to increase the accuracy of the placement of the laser beam pulses on the eye. The laser surgery system may limit movement of the patient in response to the forces to the eye, and may provide the measured forces to the user. In many embodiments, the patient interface may comprise a compliance that allows the eye to move when coupled to the interface so as to decrease pressure to the eye, and the laser eye surgery system can offset the laser beam pulses in one or more of three dimensions in response to the measured forces and the compliance so as to increase accuracy of the focused laser beam on the eye.

In a first aspect, a laser eye surgery comprising a patient support, a patient interface, and a controller is provided. The patient interface couples to the eye of a patient and comprises an axis alignable with the eye of the patient. The patient interface further comprises a plurality of force transducers to monitor forces between the eye of the patient and the patient interface. The controller is coupled to the support to move the at least one of the patient support or the patient interface in response to the monitored forces. The patient support or the patient interface can be moved along the axis and transverse to the axis. In many embodiments, the patient support is moved while the patient interface remains stationary or vice versa. Typically, the patient support will be moved while the patient interface remains stationary.

The patient support will typically comprise a base and a linkage to move the patient support along the axis and transverse to the axis in response to the controller. For instance, the patient support may comprise a moveable patient chair having a patient seating area moveable relative to the base.

There will typically be at least three force transducers coupled to the controller. Each force transducer monitors a force between the eye of the patient and the patient interface. Typically, the controller is configured to receive the force from each of the force transducers and determine (1) a force along the axis of the patient interface, (2) a first force in a first direction transverse to the axis, and (3) a second force in a second direction transverse to the axis, i.e., forces along the X, Y, and Z axes. The laser eye surgery system may further comprise a display for displaying the calculated forces along the axis, the first direction, and the second direction as a three dimensional vector. The controller may embody instructions of a program to move the patient support along X, Y, and Z axes in response to the calculated forces so as to maintain the forces between the eye of the patient and the patient interface within a desired range. The controller may also embody instructions of a program to offset pulses of the laser beam in response to forces of the plurality of transducers or to allow movement of the patient support along the X and Y directions transverse to the Z axis to decrease force to the eye.

The laser eye surgery system may further comprise a counter-weight coupled to the patient interface. The counter-weight facilitates vertical movement of the patient interface.

In many embodiments, the axis of the patient interface extends in a vertical direction and the patient interface is adapted to move upward by upward movement of the patient support when the patient is placed on the patient support and the eye of the patient is coupled to the patient interface.

The laser eye surgery system may comprise a locking mechanism adapted to lock the vertical position of the patient interface when the patient interface has reached a desired vertical position. The locking mechanism may comprise one or more of a detent, a lock and key mechanism, an opening to receive a linear protrusion, a rotating cam, or a flat surface to receive a friction brake.

In another aspect, a method of coupling an eye of a patient relative to a patient interface is provided. The patient is placed on a moveable patient support; the eye of the patient is coupled to the patient interface to align an axis of the patient interface with the eye; and the patient support is moved along the axis with the eye to position the patient interface for surgery. Often, a vertical position of the patient interface is tracked and the upward movement of the moveable patient support is limited based on the tracked vertical position of the patient interface.

The eye may be coupled to the patient interface by coupling a suction ring to the eye and coupling the suction ring to a disposable lens cone coupled to the patient interface.

The patient interface will typically be locked in place once the patient support has reached the desired vertical position. When the patient interface has been locked in place, upward movement of the moveable patient support will typically be limited by preventing any further upward movement of the moveable patient support. The lateral movement of the moveable patient support will typically be unrestricted while the upward movement of the moveable patient support is limited. In some embodiments, however, the lateral position of the patient interface is tracked and lateral movement of the patient support is limited based on this tracked lateral position.

In another aspect, a method of stabilizing an eye of a patient relative to a patient interface of a laser eye surgery system is provided. A patient is placed on a top side of a moveable patient support of the laser eye surgery system; the eye is coupled to the patient interface positioned above the eye; vertical forces are monitored between the patient interface and the eye; and the patient interface is moved with the eye to position the interface and the eye for surgery. The eye will typically be coupled to the patient interface by coupling a suction ring to the eye and coupling the suction ring to a disposable lens cone coupled to the patient interface. The monitored vertical forces will often be displayed on a display coupled to the laser eye surgery system.

Generally, the patient interface moves vertically while maintaining a substantially constant vertical force between the patient interface and the eye. Vertically moving the patient support may comprise operating a user controlled control element of the laser eye surgery system to vertically move the patient interface based on the displayed vertical forces. The user controlled control element may be, for example, a joy stick or a touch screen control panel. In many embodiments, the patient support is instead automatically moved based on the monitored vertical forces to maintain constant vertical force between the patient interface and the eye.

The provided method may further comprise a step of calculating lateral forces between the patient interface and the eye based on the monitored vertical forces. The patient support may be moved laterally to maintain the lateral forces within a desired range. The calculated lateral forces will often be displayed on a display coupled to the laser eye surgery system. To keep the lateral forces within a desired range, an operator of the laser eye surgery system may operate a user controlled control element of the laser eye surgery system to laterally move the patient interface based on the displayed lateral forces. The user controlled control element may comprise, for example, a joystick or a touch screen control panel. In many embodiments, the patient support is instead automatically moved based on the calculated lateral forces to keep the lateral forces within a desired range.

In another aspect, a method of treating an eye of a patient is provided. The patient is placed on a moveable patient support; the eye is coupled to a patient interface of a laser eye surgery system; forces are measured between the patient interface and the eye; determining movement of the eye location is determined based on the measured forces and stiffness of the patient interface; and laser target locations are adjusted based on the determined movement. Movement of the eye may be determined by determining movement of a targeted location of the eye and calculating relative movement of the targeted location of the eye based on the eye's stiffness characteristics.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Methods and systems related to laser eye surgery are disclosed. A laser is used to form precise incisions in the cornea, in the lens capsule, and/or in the crystalline lens nucleus, for example. The embodiments of the present disclosure as described herein are particularly well suited for beneficial combination with one or more surgical procedures such as cataract surgery, refractive surgery, retinal surgery, intraocular lenses, intracorneal lenses, corneal sculpting, Laser-Assisted in Situ Keratomileusis (hereafter "LASIK"), or laser-assisted subepithelial keratomileusis (hereinafter "LASEK), and combinations thereof, for example. The surgical laser system as described herein may comprise a patient interface assembly configured to inhibit increases of intraocular pressure during surgery, can facilitate alignment during surgery, and can provide improved alignment of the patient. The patient interface may comprise an axis for alignment with an axis of the eye such as an optical axis of the eye. The patient interface may comprise a guide to allow the patient interface to move along the axis with the eye. The patient interface may comprise a lock to hold the patient interface at a location along the axis. The patient interface may comprise a plurality of transducers to measure forces to the eye during surgery, and the laser surgery system can limit movement of the patient in response to the forces to the eye, and may offset the position of the laser beam pulses in response to the measured forces.

System Configuration

Figure 1:
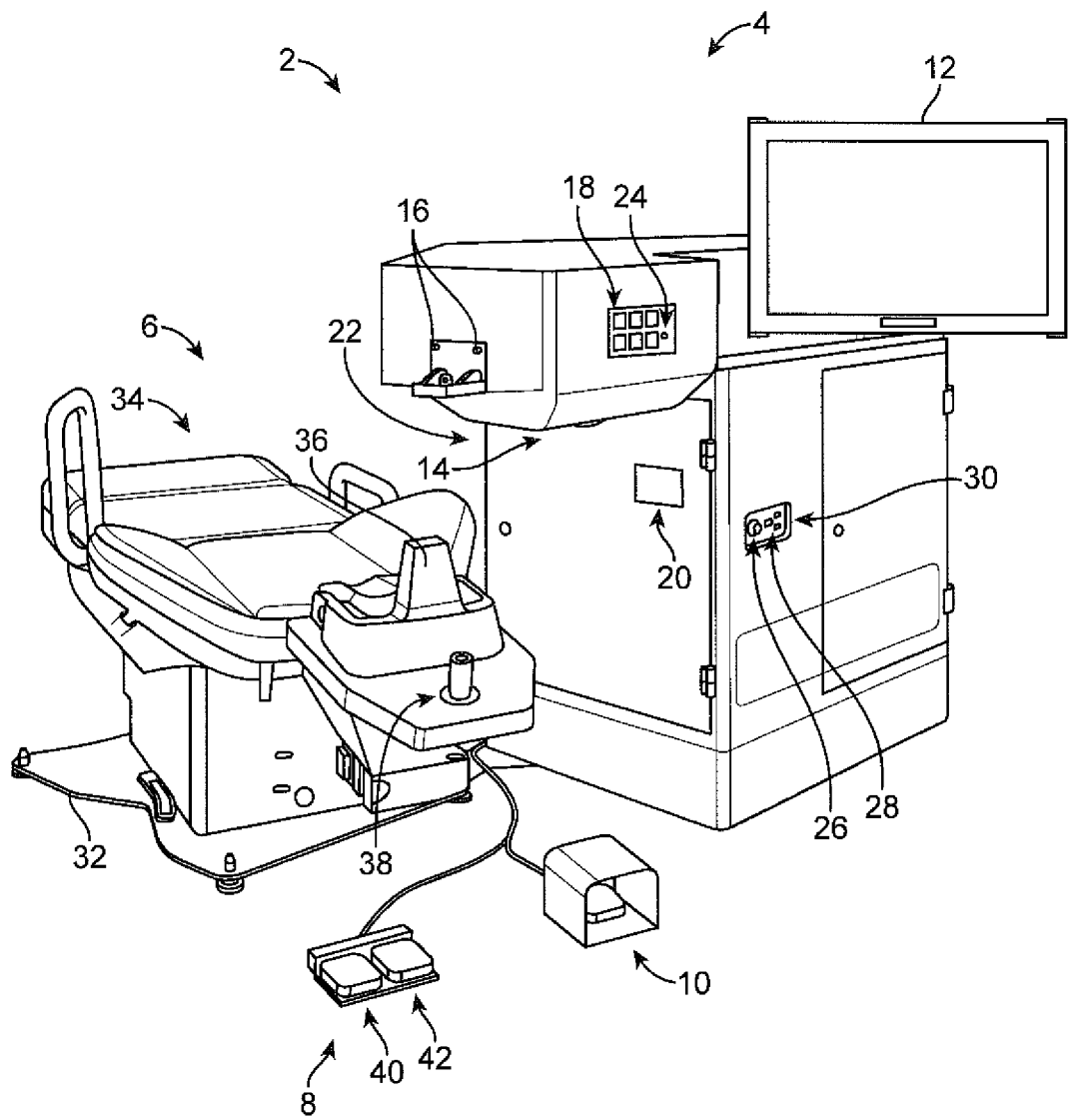
FIG. 1 is a perspective view showing a laser eye surgery system, in accordance with many embodiments.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38. To further protect against unintended chair motion, power supplied to the patient chair 6 may automatically be cut off using a switch.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user is without access to network based printing.

Figure 2:
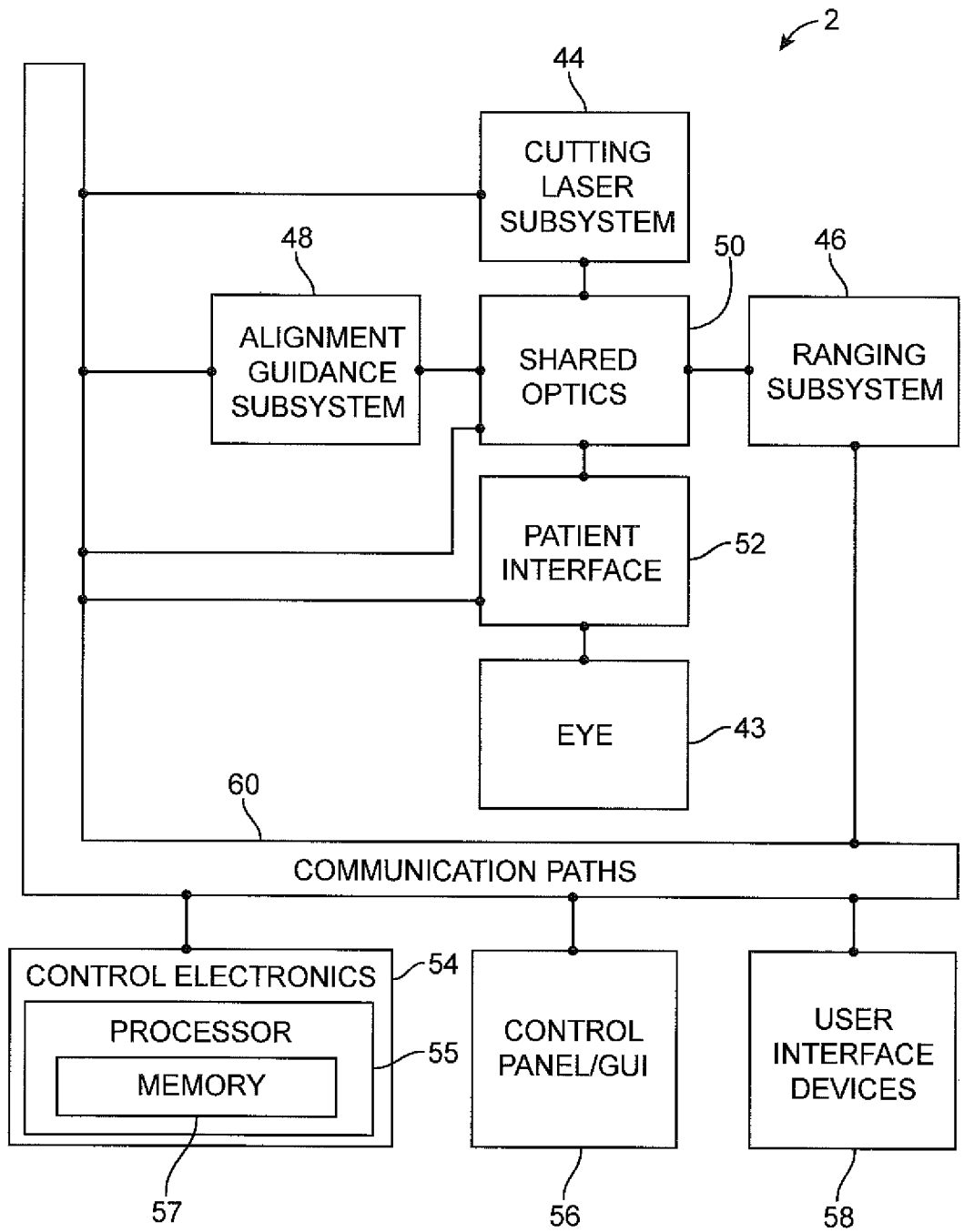
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, the ranging subsystem 46, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
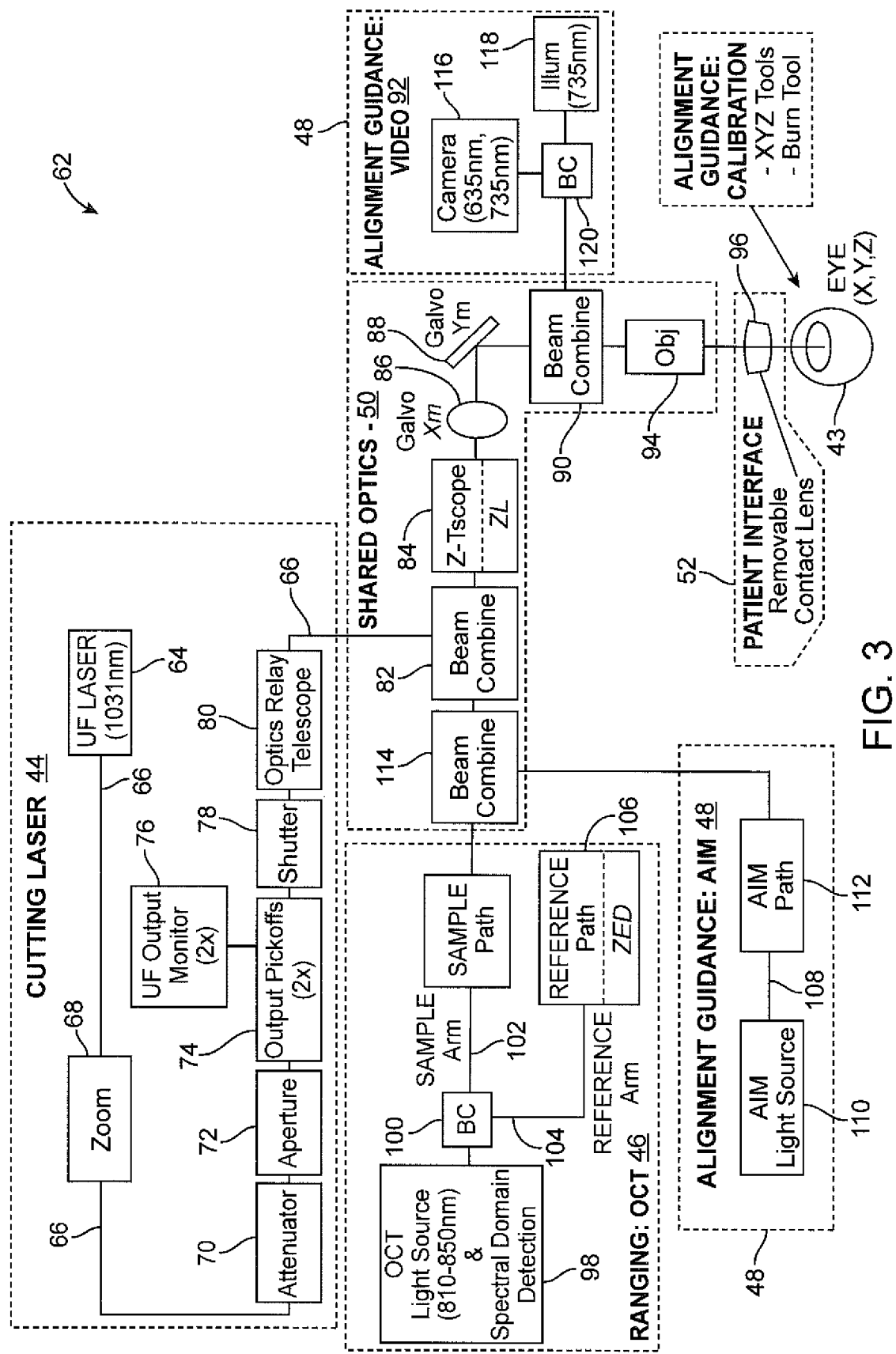
FIG. 3 is a simplified block diagram illustrating the configuration of an optical assembly of a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/− 5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED, 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof; such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source may be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be an suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 4:
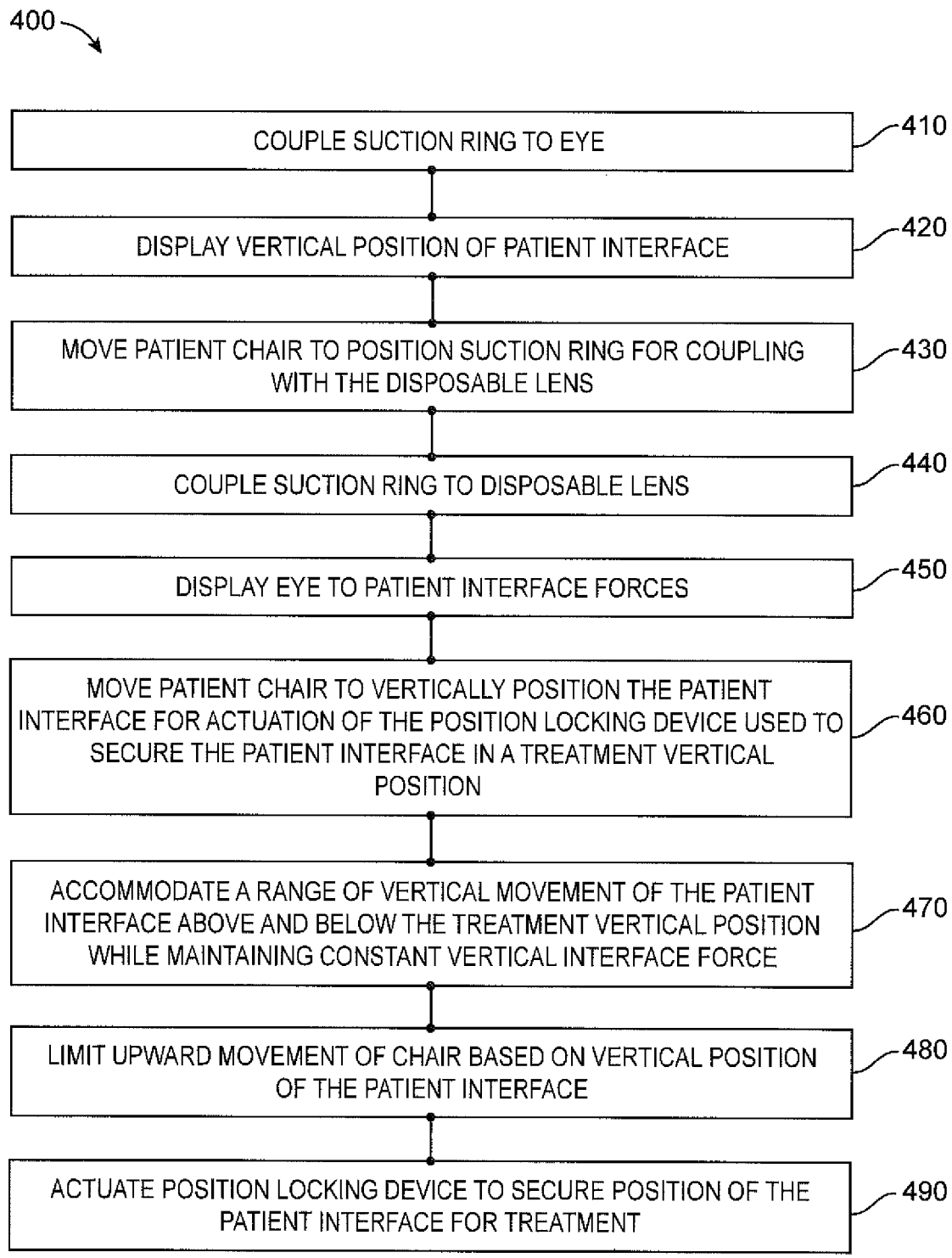
FIG. 4 is a flow chart illustrating a procedure to secure the position of the patient's eye relative to the patient interface, in accordance with many embodiments.

FIG. 4 is a flow chart of a method 400 in which force feedback is used to secure a patient to the patient interface 52 of the laser eye surgery system 2, according to embodiments of the present invention. In a step 410, a suction ring, for example suction ring 122 described below, is coupled to the patient's eye 43. In a step 420, the vertical position of the patient interface 52 of the laser eye surgery system 2 is displayed, for example, on the touch-screen control panel 12, any display connected to the external connections 22 or USB data ports 30, and/or the control panel/GUI described above. In a step 430, the patient chair 6 of the laser eye surgery system 2 is moved to position the suction ring for coupling with a disposable lens cone, for example disposable lens cone 124 described below. In a step 440, the suction ring is coupled to the disposable lens. In a step 450, the magnitudes and directions of the eye-to-patient interface forces are displayed, for example, on the touch-screen control panel 12, any display connected to the external connections 22 or USB data ports 30, and/or the control panel/GUI described above. These eye-to-patient interface forces are measured and calculated for as described below and will typically include forces in the vertical as well as lateral directions. In a step 460, the patient chair 6 is moved to vertically position the patient interface 52 for actuation of a position locking device 126 used to secure the patient interface 52 in a desired treatment vertical position. In a step 470, a range of vertical movement of the patient interface 52 above and below the treatment vertical position is accommodated while constant vertical force between the patient's eye 43 and the interface 52 is maintained. In a step 480, the upward movement of the patient chair 6 is limited based on the vertical position of the patient interface 52. In a step 490, the position locking device 126 is actuated to secure the position of the patient interface 52 for treatment.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

FIGS. 5A-5E show a method by which the patient's eye 43 is secured to the patient interface 52 of the laser eye surgery system 2 according to embodiments of the present invention.

Figure 5A:
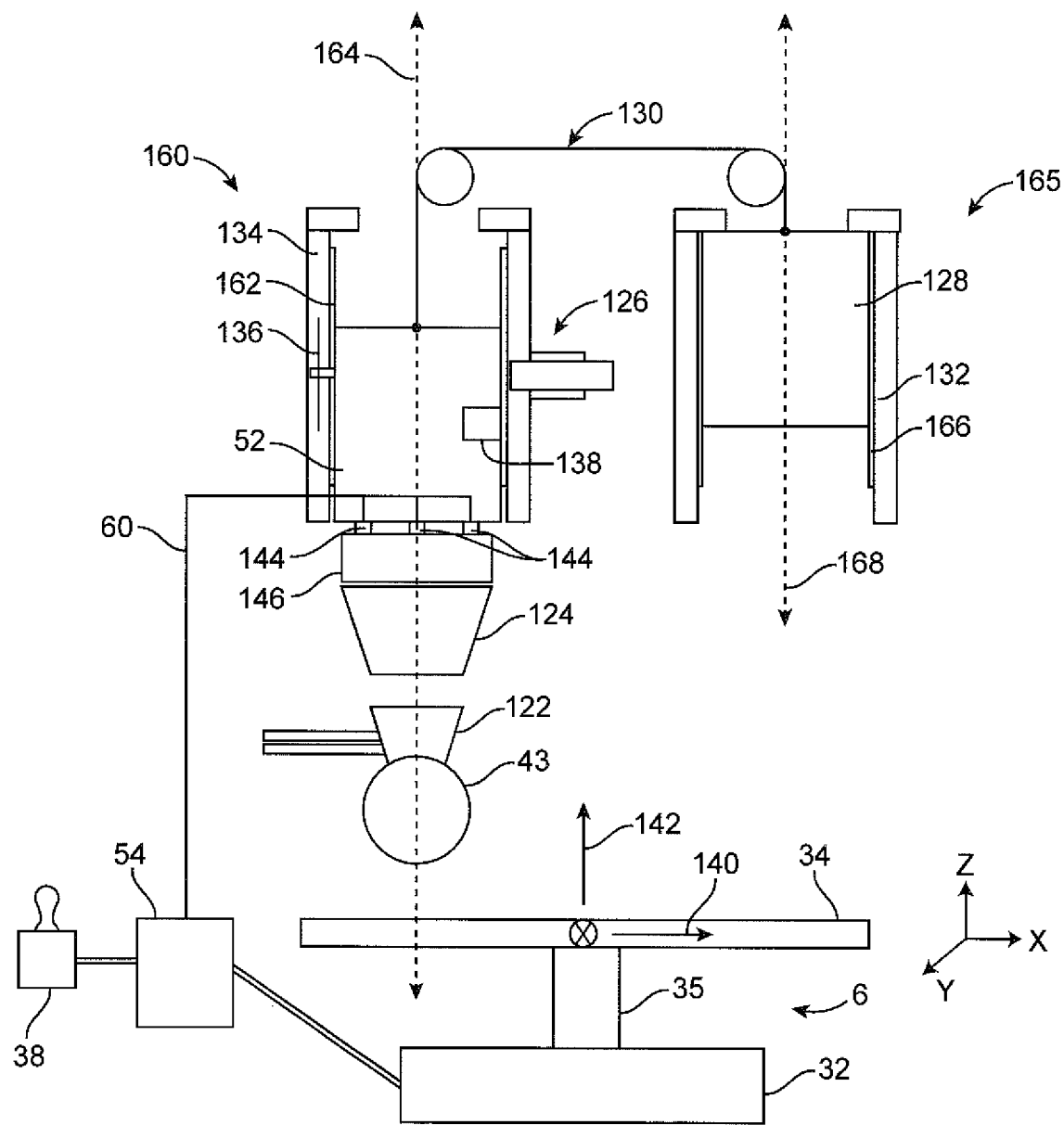
FIGS. 5A-5E show the securing of the position of the patient's eye relative to the patient interface, in accordance with many embodiments.

FIG. 5A shows a preliminary step of coupling the patient's eye 43 with a suction cup 122. The patient will typically be resting on a top side of the patient support bed 34, which as shown by arrow 140 can be moved laterally in both the X and Y directions as well as vertically in the Z direction as shown by arrow 142. The suction cup 122 may comprise an annular vacuum ring to couple to the eye with suction and a second vacuum line to apply suction to a lens placed over the eye.

The patient interface 52 may comprise a component of a patient interface assembly 160. The patient interface assembly 160 may comprise the housing 134, the patient interface 52, and the counterweight 128, for example. The patient interface assembly may comprise a guide 162, for example a guide formed with a channel in the housing, so as to allow movement of the patient interface along an axis 164, typically a vertical axis. Such vertical movement is facilitated by a counterweight 128 which is housed within 132 and coupled to the patient interface 52 via cable assembly 130. The counterweight 128 may comprise a component of a counterweight assembly 165 which may comprise the housing 132 and a guide 166 so as to allow movement of the counterweight 128 along an axis 168, typically a vertical axis. The housing 134 of the patient interface assembly 160 also comprises a linear encoder 136 to determine the vertical position of the housing assembly 52. The housing 134 further comprises a locking mechanism 126 which can be actuated to lock the patient interface 52 at a desired vertical position. In many embodiments, the counterweight 128 biases the patient interface 52 to be at this desired vertical position. When the patient interface 52 is at the desired vertical position, the locking mechanism 126 can lock into receptacle 138 in the patient interface 52. The locking mechanism 126 may comprise one or more of a detent, a lock and key mechanism, an opening to receive a linear protrusion, or a rotating cam, a flat surface to receive a friction brake. The friction brake may be configured to break free from the flat surface if the vertical force from the patient interface 52 surpasses a threshold limit that would be considered dangerous to the patient. The patient interface 52 comprises a disposable lens cone 124 which is configured to couple to the suction cup 122. The disposable lens cone 124 is coupled to the main body of the patient interface 52 via coupler 146. The patient interface 52 comprises a plurality of force transducers 144 disposed between the main body of the patient interface 52 and the coupler 146. Typically, the force transducers 144 will lie in the same horizontal plane normal to the vertical axis 164 of the patient interface 52 and parallel to the suction cup 122 and the disposable lens cone 124. The force transducers 144 detect the amount of vertical force between the main body of the patient interface 52 and the coupler 146, including the force between the patient interface 52 and the patient's eye 43, when the suction cup 124 is coupled to both the patient's eye 43 and the disposable lens cone 124. The force transducers 144 can transmit data regarding measured force via communications paths 60 to the other subsystems of the laser eye surgery system 2 including the control electronics 54, the control panel/GUI 56, and the user interface devices 58.

Figure 5B:
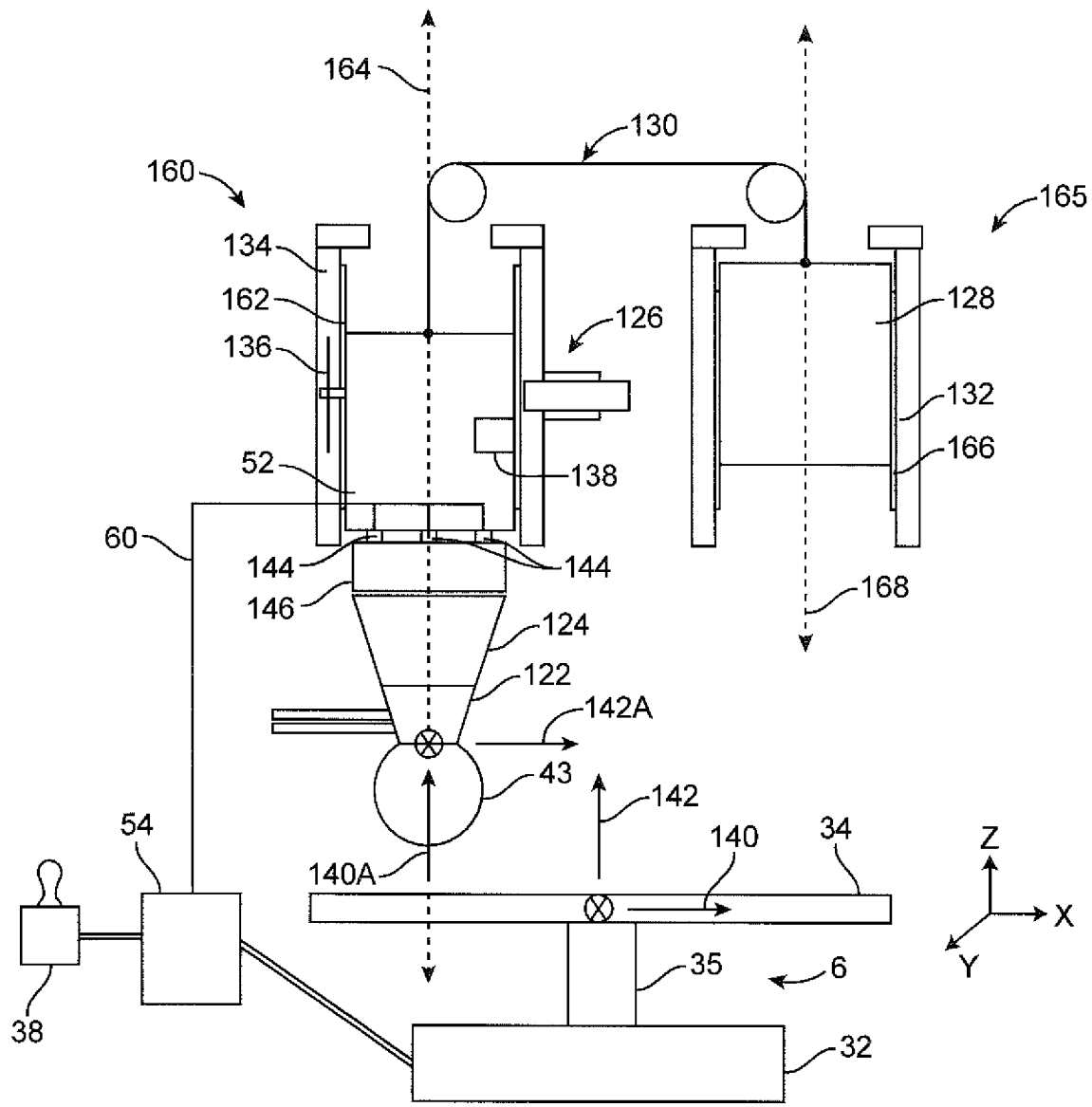

As shown in FIG. 5B, once the suction cup 122 is coupled to the patient's eye 43, the suction cup 122 can be coupled to the disposable lens cone 124 to couple the patient's eye 43 to the interface assembly 52. Because the patient is resting on and secured to the patient support bed 36, the position of the patient's eye 43 can be varied laterally in the X and Y directions as shown by arrow 142A as well as in the vertically in the Z direction as shown by arrow 140A by varying the position of the patient support bed 34 relative to the base 32, for example, by adjusting the patient chair joystick control 38 which adjusts a linkage 35 of the patient chair 6.

Figure 5C:
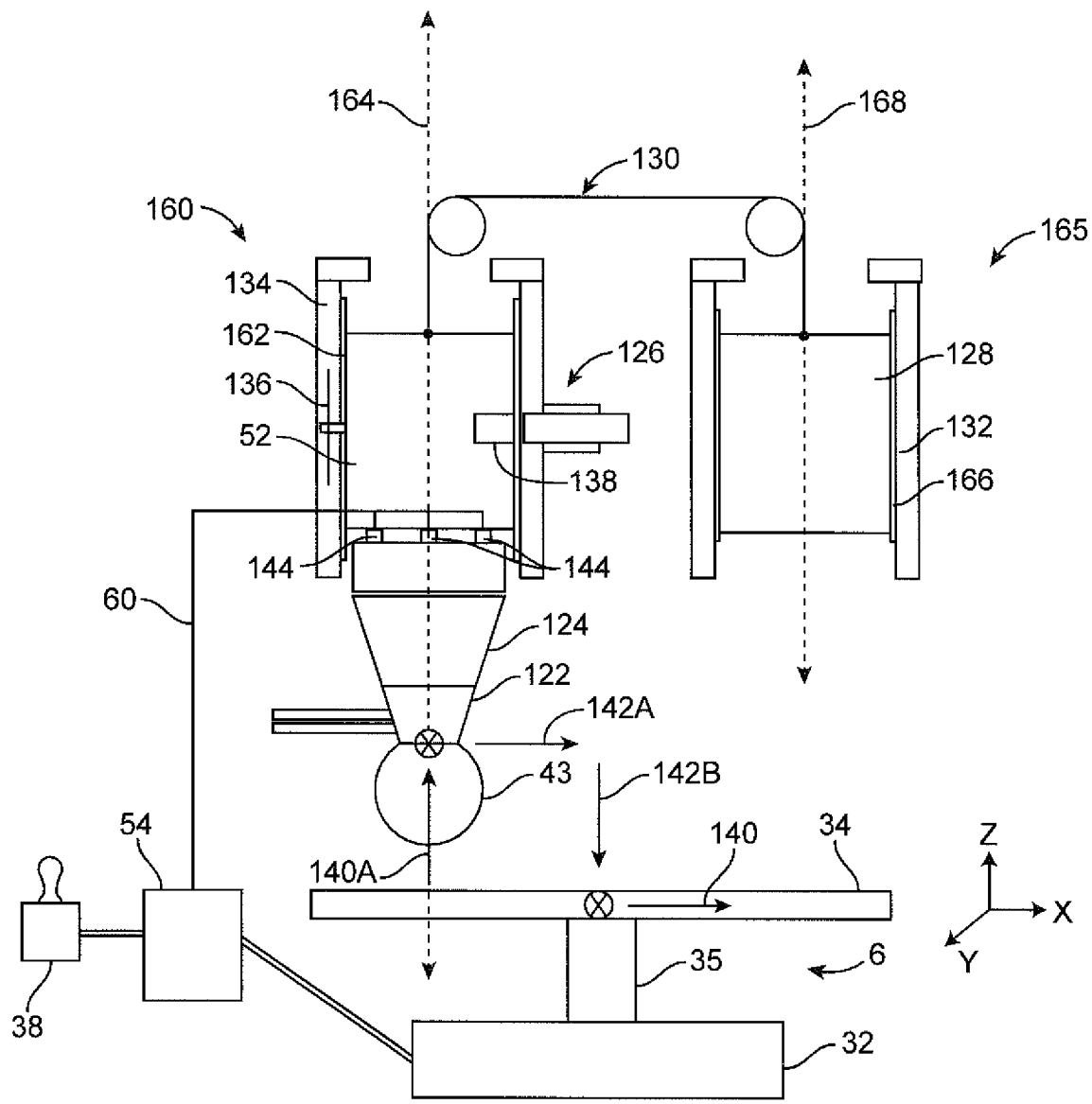

As shown in FIG. 5C, the patient interface 52 can be moved vertically and locked in place at a desired position by actuating locking mechanism 126. The patient is seated onto the patient support bed 36 and the patient's eye 43 is coupled the patient interface 52 so that the patient interface 52 will typically be moved upward by moving the patient support bed 36 upward. When the linear encoder 136 detects that the patient interface 52 is in the desired vertical position, the linear encoder 136 will send a signal to the control electronics 52 to indicate that the patient interface 52 is in the desired vertical position. The locking mechanism 126 may then lock the patient interface 52 in the desired vertical position. The control electronics 54 may then limit or prevent further upward movement of the patient support bed 34 to prevent any injury to the patient's eye 34 that may occur if the patient support bed 34 is moved up while the patient interface 52 remains in place, which would otherwise sandwich the patient's eye 43. While the patient support bed 34 is limited or prevented from further upward movement, lateral movement of the patient support bed 34 will typically be unrestricted.

The patient interface 52 comprises at least three force transducers 144. The force transducers 144 measure force in the Z-direction. Because there will typically be at least three force transducers 144, the force differential between the transducers can be used to calculate the magnitude and direction of the forces between the patient interface 52 and the patient's eye 43 in the X, Y, and Z directions. For example, the patient interface 52 may send the force data from the force transducers 144 to the control electronics 54 which in turn calculates the force between the patient interface 52 and the patient's eye 43 in the X, Y, and Z directions. As discussed above with regard to method 400, the calculated patient interface to eye forces can be displayed and the laser eye surgery system operator can adjust the position of the patient support bed 36 via patient chair joystick control 38 so that the patient interface to eye forces remain constant over the course of a laser eye surgical procedure. For example, the laser surgery system operator can view the displayed forces and through the patient chair control input device 38, adjust the position of the patient support bed 36. In many embodiments, this procedure can be automated. For example, the control electronics 52 may calculate the patient interface to eye forces in the X, Y, and Z directions and automatically adjust the position of the patient support bed 36 accordingly as in method 900 described below.

Figure 5D:
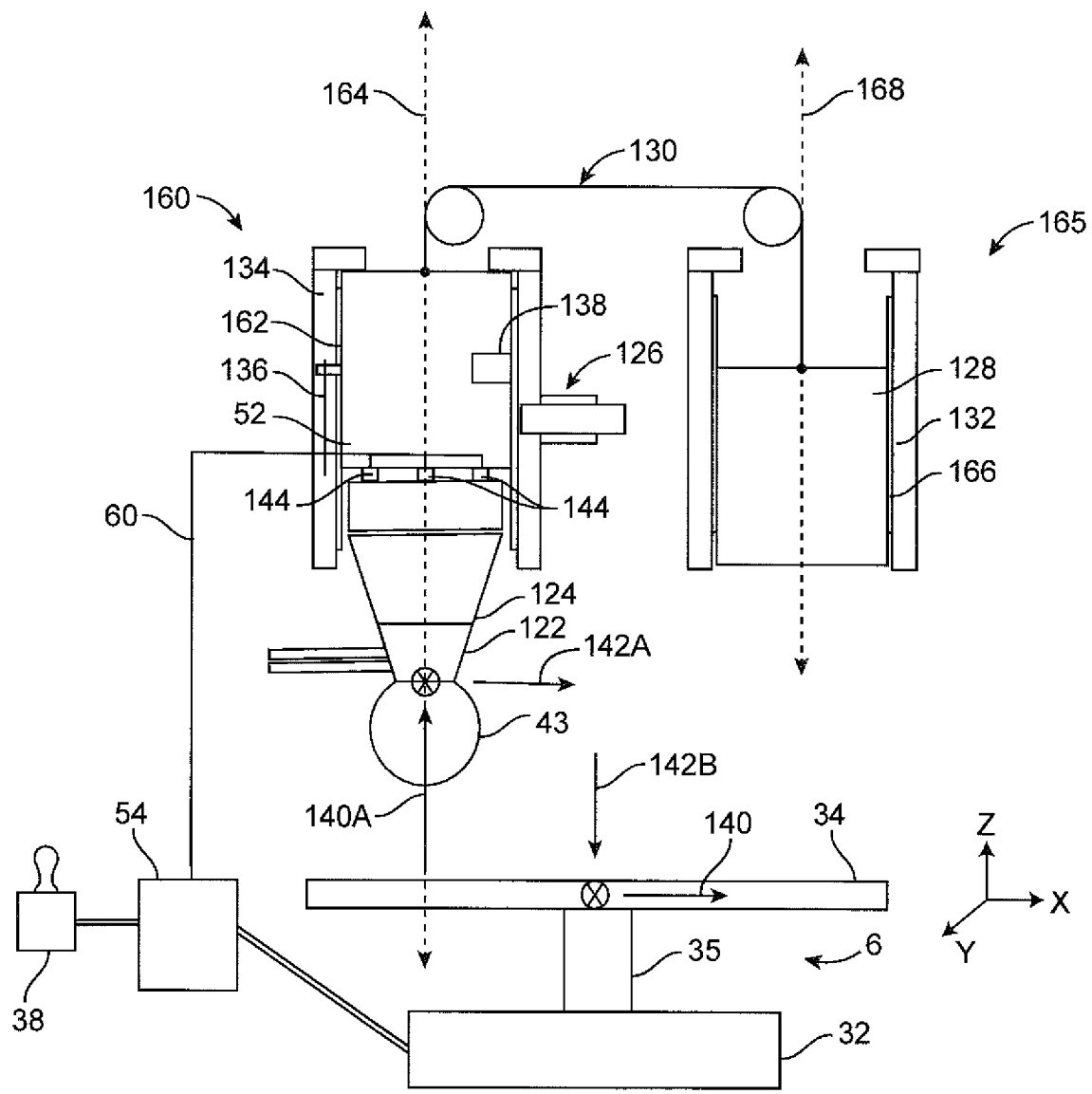

As shown in FIG. 5D, the patient interface 52 can be moved upward within the housing 134 beyond the position the patient interface 52 would be in if locked into position by locking mechanism 126, giving the patient interface 52 some vertical leeway within the housing 134 as the patient interface 52 is moved into the desired vertical position.

Figure 5E:
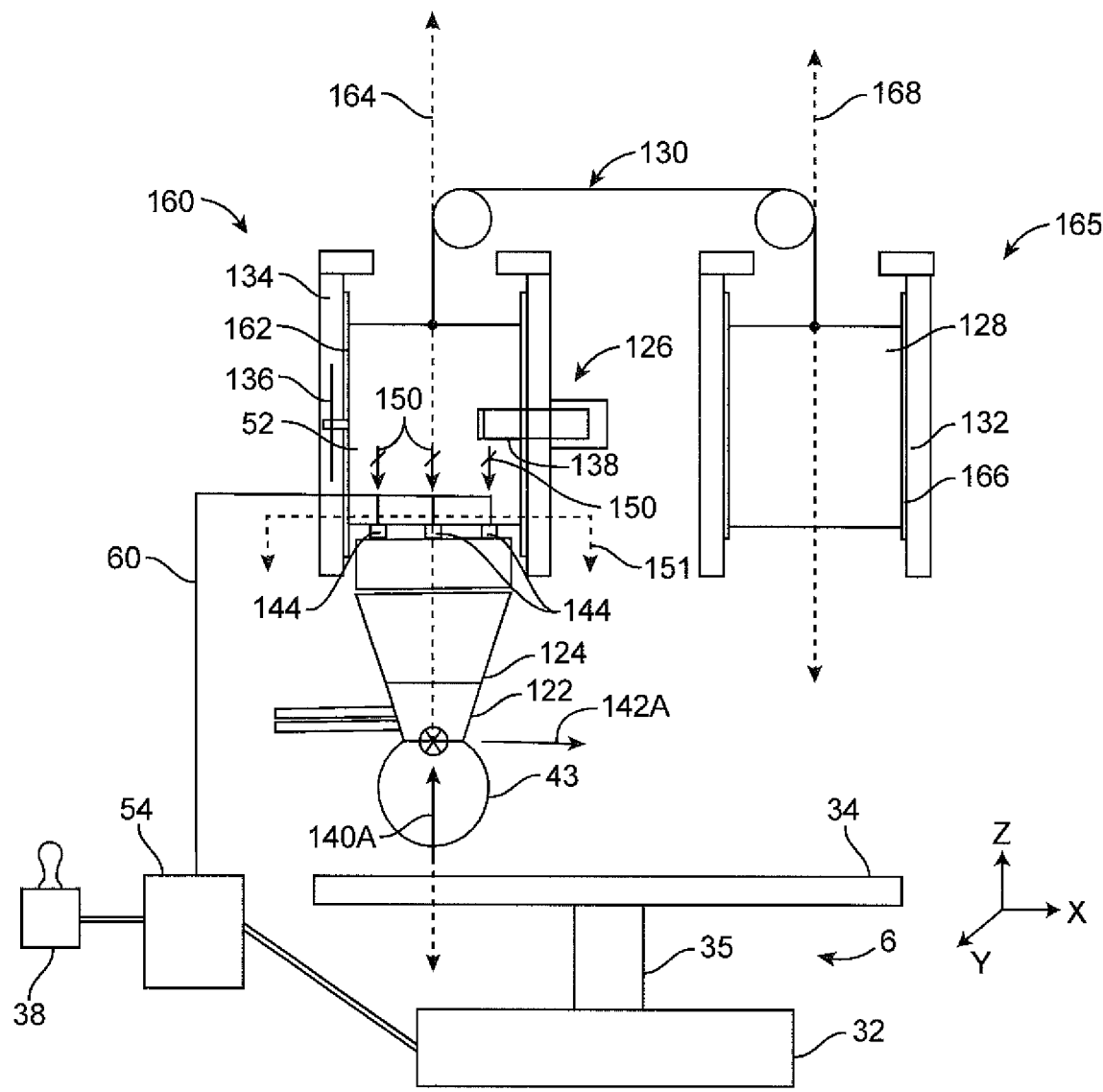

FIG. 5E shows the patient interface 52 locked into the desired vertical position by locking mechanism 126. As discussed above, the force transducers 144 detect the vertical forces (represented by arrows 150) between the patient interface 52 and the patient's eye 43.

Figure 6:
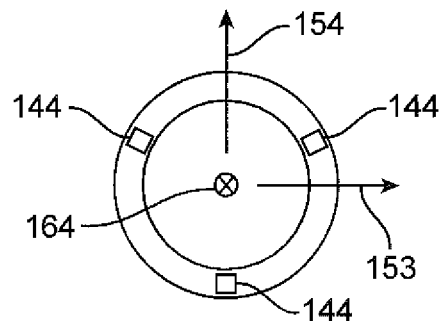
FIG. 6 shows a cross-section of the patient interface, in accordance with many embodiments.

FIG. 6 shows a cross-section of the patient interface 52 taken along line 151 shown in FIG. 5E. As discussed above, the patient interface 52 comprises a plurality of force transducers 144. The force transducers 144 are positioned equidistant from a central vertical axis 152 of the patient interface 52 and are equidistant from one another as well. The force transducers 144 measure the forces between the patient interface 52 and the patient's eye 43 along the vertical axis 164. The force differentials between the force transducers 144 are used to calculate the lateral forces between the patient interface 52 and the patient's eye 43, i.e., the X-direction as shown by arrow 153 and the Y-direction as shown by arrow 154.

Figure 7:
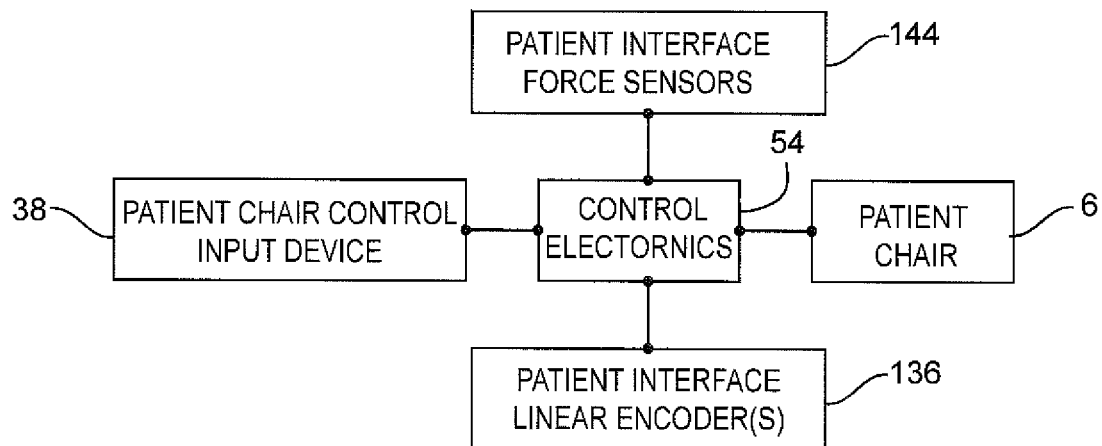
FIG. 7 is a simplified block diagram of a subsystem to monitor and control the position of the patient's eye relative to the patient interface, in accordance with many embodiments.

FIG. 7 is a simplified block diagram of subsystem of the laser eye surgery system 2 used to monitor and control the position of the patient's eye relative to the patient interface. The patient interface force sensors 144 are coupled to the control electronics 54. As discussed above, the patient interface force sensors 144 measure forces and send the measurement data to the control electronics 54. The patient interface linear encoder 136 tracks the vertical position of the patient interface 52 and sends the position data to the control electronics 54. The control electronics 54 may then send the force and position data to another subsystem of the laser eye surgery system 2 to be displayed to the operator of the laser eye surgery system 2. The control electronics 54 are also coupled to the patient chair control input device 38, which will typically be a joystick, and also to the patient chair 6. The operator of the laser eye surgery system 2 can send instructions through the control electronics to adjust the position of the patient chair 6. As discussed above with regard to FIG. 5C, the position of the patient chair 6 can be adjusted so the forces and vertical position of the patient interface 52 relative to the patient's eye 43 can be held substantially constant over the course of a laser eye surgical procedure.

Figure 8:
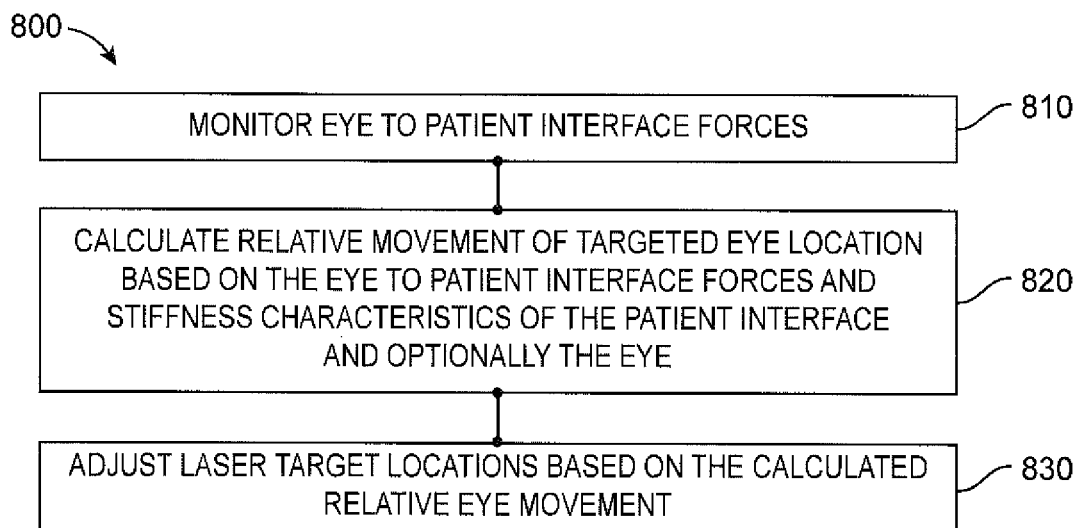
FIG. 8 is a flow chart illustrating a procedure to adjust the laser eye surgery system, in accordance with many embodiments.

FIG. 8 is a flow chart illustrating a procedure 800 to adjust the laser eye surgery system 2. In addition to measuring forces in three dimensions and the vertical position of the patient interface 52, the patient interface 52 and its force transducers 144 can be used to determine the movements of the patient's eye 43 and the laser eye surgery system 2 can be adjusted accordingly. In a step 810, the eye to patient interface forces are monitored. In a step 820, the relative movement of a targeted eye location is calculated based on the eye to patient interface forces and stiffness characteristics of the patient interface and optionally the eye. In a step 830, the laser target locations are adjusted based on the calculated relative eye movement.

Figure 9:
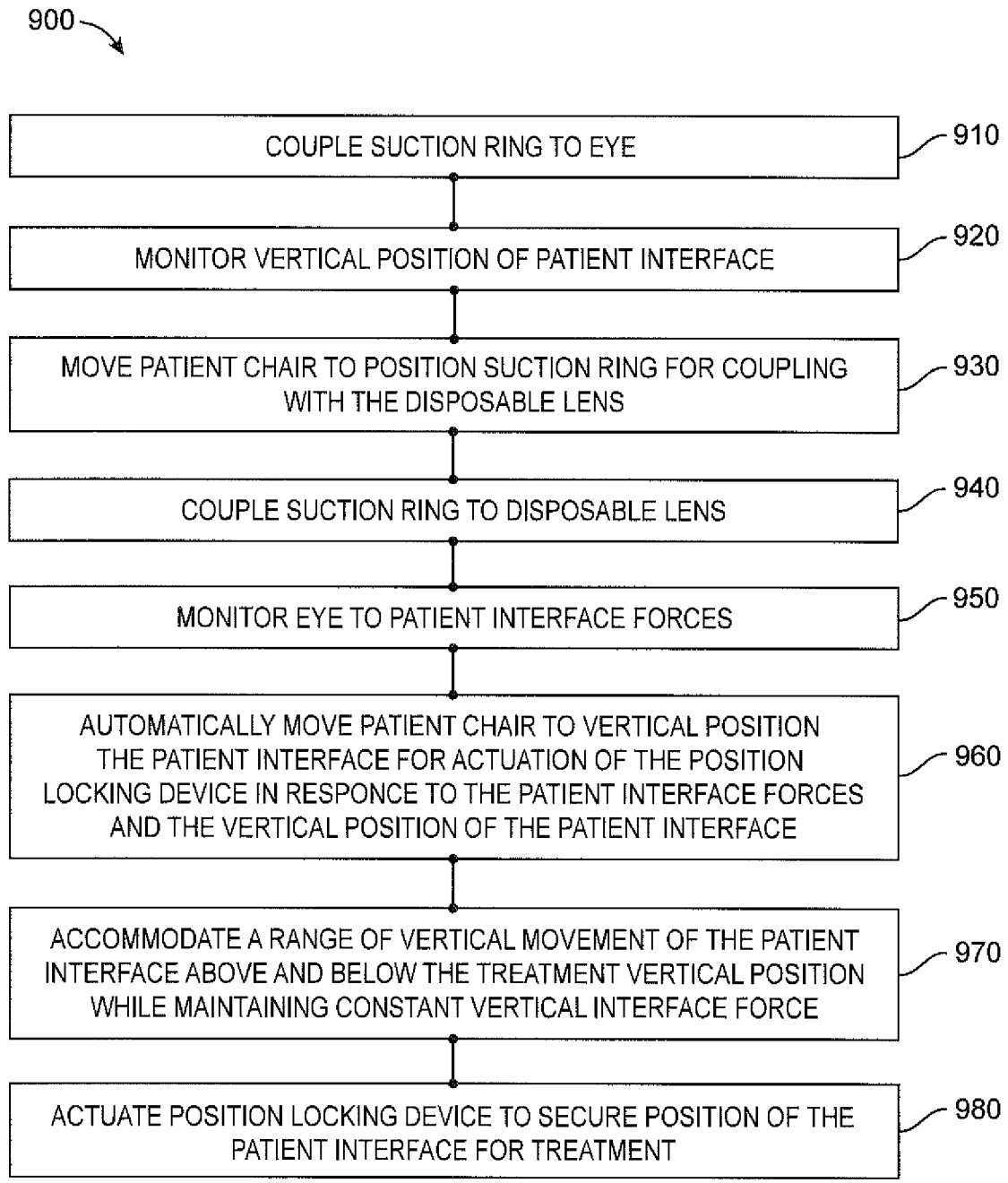
FIG. 9 is a flow chart illustrating a procedure to secure the position of the patient's eye relative to the patient interface, in accordance with many embodiments.

FIG. 9 is a flow chart illustrating a method 900 to position of the patient's eye 43 relative to the patient interface 52. As discussed above with reference to FIG. 5C, the control electronics 52 of the laser eye surgery system 2 may calculate the magnitudes and directions of the patient interface to eye forces and automatically adjust the position of the patient support bed 36 accordingly. FIG. 9 shows a method 900 in which such calculation and automatic adjustment is performed. In a step 910, the suction ring 122 is coupled to the patient's eye 43. In a step 920, the vertical position of the patient interface 52 is monitored. In a step 930, the patient chair 6 is moved to position the suction ring 122 for coupling with the disposable lens 124. In a step 940, the suction ring 122 is coupled to the disposable lens 940. In a step 950, the eye to patient interface forces are monitored. In a step 960, the patient chair 6 is automatically moved to vertically position the patient interface 52 for actuation of the position locking device 126 in response to the patient interface forces and the vertical position of the patient interface 52. In a step 970, a range of vertical movement of the patient interface 52 is accommodated above and below the treatment vertical position while maintaining a constant vertical interface force. In a step 980, the position locking device 126 is actuated to secure the position of the patient interface 52 for treatment of the patient. As discussed above, when the patient interface 52 is secured, the further upward movement of the patient chair 6 may be limited or restricted to prevent injury to the patient's eye while lateral movement of the patient chair 6 remains unrestricted.

Although the above steps show method 900 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 900 may be performed with the circuitry as described herein, for example one or more of the processor or logic circuitry such as the programmable array logic for field programmable gate array. The circuitry may be programmed to provide one or more of the steps of method 900, and the program may comprise program instructions stored on a computer readable memory or programmed steps of the logic circuitry such as the programmable array logic or the field programmable gate array, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of coupling an eye of a patient relative to a patient interface, the method comprising:
   placing the patient on a moveable patient support;
   coupling the eye of the patient to the patient interface to align an axis of the patient interface with the eye;
   moving the patient support or the patient interface along the axis with the eye to position the patient interface for surgery;
   tracking a vertical position of the patient interface using an encoder; and
   limiting movements of the moveable patient support or the patient interface based on the tracked vertical position of the patient interface.

2. The method of claim 1, wherein coupling the eye to the patient interface comprises coupling a suction ring to the eye and coupling the suction ring to a disposable lens cone coupled to the patient interface.

3. The method of claim 1, further comprising locking the patient interface in place once the patient support has reached a desired vertical position.

4. The method of claim 1, wherein limiting movements of the moveable patient support or the patient interface comprises preventing further upward movement of the moveable patient support when the patient interface has been locked in place.

5. The method of claim 1, further comprising coupling a counter-weight to the patient interface to facilitate the vertical motion of the patient interface.

6. A method of coupling an eye of a patient relative to a patient interface, the method comprising:
   placing the patient on a moveable patient support;
   coupling the eye of the patient to the patient interface to align an axis of the patient interface with the eye;
   moving the patient support or the patient interface along the axis with the eye to position the patient interface for surgery;
   wherein a lateral movement of the moveable patient support or the patient interface is unrestricted while an upward movement of the moveable patient support or the patient interface is limited.

7. The method of claim 1, further comprising tracking a lateral position of the patient interface and limiting lateral movement of the patient support based on the tracked lateral position of the patient interface.

8. A method of stabilizing an eye of a patient relative to a patient interface of a laser eye surgery system, the method comprising:
   placing a patient on a top side of a moveable patient support of the laser eye surgery system;
   coupling the eye to the patient interface positioned above the eye;
   monitoring vertical forces between the patient interface and the eye; and
   moving the patient support or the patient interface with the eye to position the interface and the eye for surgery,
   wherein the patient support or the patient interface is automatically moved based on the monitored vertical forces to maintain constant vertical force between the patient interface and the eye.

9. The method of claim 8, further comprising displaying the monitored vertical forces on a display coupled to the laser eye surgery system.

10. The method of claim 8, further comprising calculating lateral forces between the patient interface and the eye based on the monitored vertical forces.

11. The method of claim 10, further comprising laterally moving the patient support to maintain the lateral forces within a desired range.

12. The method of claim 11, further comprising displaying the calculated lateral forces on a display coupled to the laser eye surgery system.

13. The method of claim 12, wherein laterally moving the patient support to keep the lateral forces within a desired range comprises operating a user controlled control element of the laser eye surgery system to laterally move the patient interface based on the displayed lateral forces.

14. The method of claim 13, wherein the user controlled control element comprises a joystick.

15. The method of claim 13, wherein the user controlled control element comprises a touch screen control panel.

16. The method of claim 8, wherein coupling the eye to the patient interface comprises coupling a suction ring to the eye and coupling the suction ring to a disposable lens cone coupled to the patient interface.

17. A method of stabilizing an eye of a patient relative to a patient interface of a laser eye surgery system, the method comprising:
   placing a patient on a top side of a moveable patient support of the laser eye surgery system;
   coupling the eye to the patient interface positioned above the eye;
   monitoring vertical forces between the patient interface and the eye;
   moving the patient support or the patient interface with the eye to position the interface and the eye for surgery; and
   calculating lateral forces between the patient interface and the eye based on the monitored vertical forces;
   wherein the patient support or the patient interface is automatically moved based on the calculated lateral forces to keep the lateral forces within a desired range.

18. A method treating an eye of a patient, the method comprising:
   placing the patient on a moveable patient support;
   coupling the eye to a patient interface of a laser eye surgery system;
   measuring forces between the patient interface and the eye;
   determining movement of the eye location based on the measured forces and stiffness of the patient interface; and adjusting laser target locations based on the determined movement.

19. The method of claim 18, wherein determining movement of the eye comprises determining movement of a targeted location of the eye and calculating relative movement of the targeted location of the eye based on stiffness characteristics of the eye.

* * * * *